United States Patent
Krüger et al.

(10) Patent No.: US 10,127,355 B2
(45) Date of Patent: Nov. 13, 2018

(54) METHOD FOR SETTING THE OPERATING PARAMETERS OF A VENTILATION SYSTEM

(71) Applicant: Drägerwerk AG & Co. KGaA, Lübeck (DE)

(72) Inventors: Thomas Krüger, Reinfeld (DE); Thomas Handzsuj, Lübeck (DE); Philipp Rostalski, Lübeck (DE)

(73) Assignee: Drägerwerk AG & Co. KgaA, Lübeck (DE)

( * ) Notice: Subject to any disclaimer, the term of this patent is extended or adjusted under 35 U.S.C. 154(b) by 227 days.

(21) Appl. No.: 15/084,894

(22) Filed: Mar. 30, 2016

(65) Prior Publication Data
US 2016/0287821 A1 Oct. 6, 2016

(30) Foreign Application Priority Data
Apr. 1, 2015 (DE) .......... 10 2015 004 164

(51) Int. Cl.
*G05D 7/00* (2006.01)
*G06F 19/00* (2018.01)
(Continued)

(52) U.S. Cl.
CPC ........ *G06F 19/3406* (2013.01); *A61B 5/4836* (2013.01); *A61M 16/021* (2017.08);
(Continued)

(58) Field of Classification Search
CPC .............. G06F 19/3406; A61B 5/4836; A61M 16/021; A61M 16/0003; G05B 13/024
See application file for complete search history.

(56) References Cited

U.S. PATENT DOCUMENTS

| | | | |
|---|---|---|---|
| 2006/0162727 A1* | 7/2006 | Biondi .......... | A61M 16/00 128/204.21 |
| 2007/0000494 A1* | 1/2007 | Banner .......... | A61B 5/0205 128/204.23 |

(Continued)

FOREIGN PATENT DOCUMENTS

| | | |
|---|---|---|
| CN | 103 52 814 A | 1/2014 |
| DE | 698 20 237 T2 | 9/2004 |
| EP | 0 969 892 B1 | 12/2003 |

OTHER PUBLICATIONS

Schranz, T. Becher, D. Schädler, N. Weiler, K. Möller, "Model-based setting of inspiratory pressure and respiratory rate in pressure-controlled ventilation", Physiol. Meas., 2014, vol. 35(3), pp. 383-397.

*Primary Examiner* — Vincent Tran
(74) *Attorney, Agent, or Firm* — McGlew and Tuttle, P.C.

(57) ABSTRACT

A method selects the setting of a first operating parameter of a ventilation system that includes devices for feeding breathing air to and removing from a patient (7), a display device (13) with a screen (15) and a computer (11). The method includes presetting a first target value range for a first ventilation parameter, calculating permissible first operating parameter values by the computer (11) for the first operating parameter, so that the first ventilation parameter value is within the target value range if a permissible first operating parameter value is set; calculating values of a preset cost function, which is a function of at least one operating parameter, by the computer (11); selecting a first operating parameter value by the computer (11), at which the value of the cost function has an optimum; and outputting the selected first operating parameter value on the screen (15) of the display device (13).

20 Claims, 9 Drawing Sheets

(51) Int. Cl.
*A61B 5/00* (2006.01)
*A61M 16/00* (2006.01)
*G16H 40/63* (2018.01)
*A61B 5/087* (2006.01)

(52) U.S. Cl.
CPC ............. *G06F 19/00* (2013.01); *G16H 40/63* (2018.01); *A61B 5/087* (2013.01); *A61M 2205/3334* (2013.01); *A61M 2205/502* (2013.01); *A61M 2205/52* (2013.01)

(56) References Cited

U.S. PATENT DOCUMENTS

| | | | | |
|---|---|---|---|---|
| 2007/0181126 A1* | 8/2007 | Tolmie | ............... | A61M 16/12 128/204.21 |
| 2008/0163872 A1 | 7/2008 | Negele et al. | | |
| 2008/0216832 A1* | 9/2008 | Carter | ............... | A61M 16/0051 128/204.21 |
| 2009/0241958 A1* | 10/2009 | Baker, Jr. | ........... | A61M 16/0051 128/204.23 |
| 2011/0041850 A1* | 2/2011 | Vandine | ........... | A61M 16/0051 128/204.23 |
| 2012/0055479 A1 | 3/2012 | Friberg et al. | | |
| 2012/0096381 A1 | 4/2012 | Milne et al. | | |
| 2012/0174926 A1* | 7/2012 | Tham | ................ | A61M 16/0045 128/204.22 |
| 2012/0247471 A1* | 10/2012 | Masic | ............... | A61M 16/0051 128/204.23 |
| 2012/0272957 A1* | 11/2012 | Chapman | ........... | A61M 16/0045 128/203.12 |
| 2012/0272964 A1 | 11/2012 | Loeser et al. | | |
| 2014/0190485 A1* | 7/2014 | Milne | ............... | A61M 16/0051 128/205.23 |
| 2015/0018648 A1* | 1/2015 | Boyer | ............... | A61M 16/1005 600/323 |
| 2015/0040905 A1* | 2/2015 | Kulstad | ........... | A61M 16/0051 128/204.23 |
| 2017/0216541 A1* | 8/2017 | Truschel | .......... | G06F 19/3481 |

* cited by examiner

METHOD FOR SETTING THE OPERATING PARAMETERS OF A VENTILATION SYSTEM

CROSS REFERENCE TO RELATED APPLICATIONS

This application claims the benefit of priority under 35 U.S.C. § 119 of German Patent Application DE 10 2015 004 164.9 filed Apr. 1, 2015, the entire contents of which are incorporated herein by reference.

FIELD OF THE INVENTION

The present invention pertains to a method for selecting the setting of at least one operating parameter of a ventilation system (also known as respiration system), which has a ventilation device for feeding and removing breathing air to and from a patient, a display device with a screen and a computer.

BACKGROUND OF THE INVENTION

Such ventilation systems are used especially in intensive care, and a number of operating parameters, for example, the inspiration pressure, the inspiration time and the expiration time, can be preset by a user, such as an anesthesiologist, in order to set the patient's ventilation in a suitable manner. However, accurate understanding of the patient's physiology is necessary for these settings in order to make it possible to assess the effect of different operating parameters on the patient. The relationships and the dynamic effects are relatively complex, and simple rules of thumb are currently frequently used to make it possible to keep this complexity under control. However, these rules often fail to meet the requirements of the complex physiological processes.

In addition, the problem arises because of the comparatively complex relationships and interactions between individual operating parameters that preset limit values for other operating parameters will change when an operating parameter is varied, so that a user of a ventilation system cannot readily assess the effect of a change made in an operating parameter on limit values for other operating parameters.

It may consequently easily happen that the change made by the user in a first operating parameter causes the limit value for a second operating parameter to change as a result and the preselected setting for this second operating parameter, which should actually remain unchanged, will lead, in an unintended manner, to an actual parameter being higher or lower than the changed limit value. This may possibly remain hidden to the user or was not recognizable at least at the time of selecting the setting for the first operating parameter.

These questionable limit values arise, among other things, from the fact that the patient's lungs are damaged, for example, in case of an excessively high inspiratory pressure or an excessively large tidal volume, i.e., an excessively large breathing air volume per breath. However, since the tidal volume is linked with both the inspiratory pressure and the inspiration time, it may happen that when only the inspiration time is changed, an initially still noncritical inspiratory pressure causes the limit of the tidal volume to be exceeded at the changed inspiration time. The inspiratory pressure set is now all of a sudden above a limit value, even though this was not the case previously.

The use of the prior-art systems known from the state of the art for setting the operating parameters of a ventilation system is comparatively complicated, and it is especially difficult to achieve a setting of the operating parameter that is optimal under boundary conditions without actual values exceeding or dropping below limit values.

SUMMARY OF THE INVENTION

Based on this, an object of the present invention is therefore to provide a method for setting the operating parameters of a ventilation system, with which the operating parameters can be set such that preset limit values are complied with and optimal selection of the parameters is achieved for the patient.

This object is accomplished according to the present invention by a method for selecting the setting of at least one first operating parameter of a ventilation system with the following steps:

a) presetting a first target value range for a first ventilation parameter;
b) calculating permissible first operating parameter values, by the computer, for the first operating parameter, so that when a permissible first operating parameter value is set, the first ventilation parameter value is within the target value range;
c) calculating the values of a preset cost function by the computer, which is a function of at least one operating parameter;
d) selecting a first operating parameter value by the computer, at which the value of the cost function has an optimum, and
e) outputting of the selected first operating parameter value on the screen of the display device.

In the method according to the present invention, the user, i.e., for example, an anesthesiologist, presets a target value range or possibly only a single target value for an operating parameter.

A "ventilation parameter" in the sense of the present invention is a parameter that describes the ventilation of the patient (patient ventilation parameters), i.e., for example, the tidal volume (volume of air fed per breath), the respiratory minute volume (volume of air fed per minute), the $CO_2$ or $O_2$ concentration in the blood of the patient, the pH value of the blood of the patient or the intrapulmonary pressure, i.e., the pressure building up in the patient's lungs.

It should be noted in connection with the term "target value range" that it is also conceivable within the framework of the present invention that the upper limit and the lower limit of the target value range coincide, i.e., are selected as identical limits. The target value range collapses in this case into a single target value, but even such a selection shall fall under the term of a target value range in the sense of step a) above.

Based on the target value range, the permissible first operating parameter values are then calculated in the method according to the present invention by the computer for the first operating parameter, a "permissible" first operating parameter value being defined such that when such a permissible first operating parameter value is set on the ventilation system, the first operating parameter value is within the target value range. The calculation of the permissible operating parameter values as well as of other parameters mentioned below can be carried out on the basis of the principles described in C. Schranz, T. Becher, D. Schädler, N. Weiler, K. Möller, "Model-based setting of inspiratory pressure and respiratory rate in pressure-controlled ventilation, Physiol. Meas., 2014, Vol. 35(3), pp. 383-397. However, it is also possible to use other mathematical models.

It should be noted in this connection that an "operating parameter" in the sense of the present invention is a parameter that directly describes the air flow to or away from the patient and/or the course of such an air flow over time and that can be set on the ventilation system (ventilation system operating parameters). An operating parameter may assume a plurality of operating parameter values within a range. Examples of operating parameters are the inspiration time ($T_{insp}$), the expiration time ($T_{exp}$) and the value of the inspiratory pressure ($P_{insp}$).

The values of a preset cost function are then calculated by the computer in the method according to the present invention, and this cost function is a function of at least one operating parameter. The cost function is defined such that its value is an indicator of how high the stress or invasiveness or discomfort is for the patient when the respective first operating parameter and ventilation parameter is set, so that, for example, a lower value for the cost function represents a lower stress for the patient.

Finally, a first operating parameter value, at which the value of the cost function has an optimum, is selected by the computer in the method according to the present invention, preferably from the permissible first operating parameter values. The "optimum" of the cost function, to which reference is being made here, may be especially a minimum (minimum value).

This selected operating parameter value and hence a corresponding setting on the ventilator would cause the target value for the ventilation parameter to be reached with minimization of the invasiveness/stress/discomfort, and this selected first operating parameter is outputted according to the present invention on the screen of the display device. An optimized value for the first operating parameter is thus displayed to the user of the ventilation system automatically, because the preceding steps are carried out by the computer.

It should, however, be noted that the selected operating parameter or operating parameters is/are not transmitted in the method according to the present invention automatically to a device for feeding and removing the breathing air to and from the patient and thus they are set on this device. Rather, an intervention is required on the part of the user, be it by actuating a transmission button or by actually transmitting the values from the screen of the display device into the input device, in order to transmit the values to the device.

A limit value is preferably preset for a second ventilation parameter in the method according to the present invention, and this limit value is between a range of allowed second ventilation parameter values and a range of non-allowed second ventilation parameter values. One or more first operating parameter limit values are calculated by the computer, the first operating parameter limit value being between a first range of first operating parameter values and a second range of first operating parameter values, so that allowed second ventilation parameter values are obtained when setting first operating parameter values from the first range, and so that non-allowed second ventilation parameter values are obtained when setting first operating parameter values from the second range. The selected first operating parameter value is then selected from among first operating parameter values from the first range in step d) of the method according to the present invention.

Thus, this preferred embodiment of the method according to the present invention makes it possible to specify a limit value for an additional or second ventilation parameter, for example, the tidal volume, when the respiratory minute volume was selected as the first ventilation parameter, so that only such first operating parameter values are subsequently taken into account, when the selected first operating parameter value is determined, whose setting on the ventilation system does not lead to the actual value exceeding or dropping below the limit value. This limit value is consequently also automatically taken into account.

Consequently, if the respiratory minute volume is selected as the first ventilation parameter, for which the target value range or target value is preset, and an upper limit value is preset for the tidal volume, for example, only such values can be selected for the inspiration time as first operating parameters at which the limit value for the tidal volume is not exceeded.

In another preferred embodiment, a diagram is generated on the screen of the display device, in which diagram an interval of the first operating parameter is plotted along a line, said interval being selected such that it at least overlaps the target value range. Furthermore, the diagram has a marker at a position along the line that corresponds to the target value.

If the respiratory minute volume was selected as the first ventilation parameter and the inspiration time was selected as the first operating parameter, an interval or a value range of the respiratory minute volume is then plotted along a line, which extends, for example, horizontally, in this embodiment, and this interval overlaps at least the target value range, but the target value range is preferably completely in the interval. In addition, a marker is generated, whose position along the line corresponds to the first target value. Finally, the selected first operating parameter value is also indicated, for example, in a field at the marker. Due to this form of representation, a user can see where the target value and hence the value of the first ventilation parameter, which is obtained when the selected first operating parameter value is set on the ventilation system, is located within the target value range.

In another preferred embodiment of this method, the computer calculates with a first operating parameter limit value the first ventilation parameter value that is obtained when setting the first operating parameter limit value, and a limit value marker is provided along the line, and the position of the limit value marker along the line corresponds to the calculated first ventilation parameter value.

Consequently, when a limit value is preset, for example, for a second ventilation parameter, such as the tidal volume, the first ventilation parameter value, i.e., a value for the respiratory minute volume, which is obtained when the first operating parameter limit value arising from the limit value is set on the ventilation system, is calculated first in this embodiment. A limit value marker, which shows to a user to what extent the selection of the first ventilation parameter, i.e., the respiratory minute volume in the selected example, is limited by a limit value for the tidal volume, is generated at the position along the line, which corresponds to this calculated first ventilation parameter value.

Finally, a first operating parameter limit can be preset for the first operating parameter, for example, for the inspiration time, and a parameter limit marker is provided along the line in the diagram, the position of said parameter limit marker along the line being calculated by the computer such that the position corresponds to the first ventilation parameter value, which is obtained when setting the operating parameter limit as the first operating parameter. A user thus sees where the value for the respiratory minute volume, which value arises from the value selected for the inspiration time, is located in relation to extreme values, which arise from limitations for, for example, the inspiration time.

In another preferred embodiment of the method according to the present invention, the ventilation system has a setting device, which is designed such that the marker can be displaced along the line by adjusting the setting device, and a changed limit value is selected by displacing the marking along the line.

Such an embodiment has the advantage that a user can change the target value, on the basis of which the cost function is calculated, by means of the diagram. This is possible, in particular, in an especially intuitive manner if limit value markers and parameter limit markers are also shown, in addition to the marker, because it is now already clear visually to what extent the marker may be displaced in such a way as not to exceed limits.

After displacing the marker by the computer, the changed first operating parameter value with which the changed target value is obtained is preferably calculated by the computer, and the changed first operating parameter value is set. The target value, on which the calculation is based, is thus varied solely by displacing the marker in the diagram.

The limit value is set to the calculated second ventilation parameter and the first operating parameter limit value is set to the changed first operating parameter value preferably when the second ventilation parameter value calculated with the changed first operating parameter value is a non-allowed second ventilation parameter. This has the advantage that a user can also adapt limit values set before by displacing the marker in the diagram.

The settings of a first operating parameter and a second operating parameter, for example, the inspiration time and the inspiratory pressure, are selected in a preferred embodiment of the method,
  wherein permissible operating parameter pairs are calculated for the first operating parameter and the second operating parameter by the computer in step b), so that the first ventilation parameter value is within the target value range when setting a permissible operating parameter pair,
  wherein the values of a preset cost function, which is a function of at least one operating parameter, are calculated by the computer in step c),
  wherein an operating parameter pair, at which the value of the cost function has an optimum, is selected by the computer in step d),
  wherein a diagram, in which an interval of the first operating parameter is plotted along a first axis, is generated on the screen by the display device, said interval being selected such that at least some of the permissible first operating parameter values are located within the interval; in which diagram an interval of the second operating parameter is plotted along a second axis, which extends at right angles to the first axis, said interval being selected such that at least some of the permissible second operating parameter values are located within the interval; and in which diagram the selected operating parameter pair is displayed in the diagram corresponding to its first operating parameter value and its second operating parameter value.

Two operating parameters are displayed simultaneously in a two-dimensional diagram in this embodiment of the method according to the present invention, and a user can immediately see where the operating parameter pair selected by the computer by optimization of the cost function is located within the preset target value ranges.

In another preferred manner, a limit value is again preset for a second ventilation parameter, and the limit value is between a range of allowed second ventilation parameter values and a range of non-allowed second ventilation parameter values. A set of operating parameter limit value pairs is calculated by the computer from a first operating parameter value and a second operating parameter value, and the operating parameter limit value pairs are between a first range of operating parameter pairs and a second range of operating parameter pairs, so that allowed second ventilation parameter values are obtained when setting operating parameter pairs from the first range, and so that non-allowed ventilation parameter values are obtained from the second range when setting operating parameter pairs from the second range.

The operating parameter pair is then selected in step d) of the above method from operating parameter pairs from the first range, and the set of operating parameter limit value pairs is displayed at positions corresponding to the values of the first and second operating parameters in the diagram.

Yet another second ventilation parameter, for example, the tidal volume, for which a limit value is preset, is also taken into account in this embodiment of the method. The computer then calculates the operating parameter pairs whose setting on the ventilation system causes this limit value just to be reached, i.e., operating parameter limit value pairs are calculated. These operating parameter limit value pairs are then displaced in the two-dimensional diagram together with the selected operating parameter pair, so that it becomes clear to the user where the selected operating parameter pair is located in relation to the operating parameter limit value pairs.

The second operating parameter can be preferably selected as the cost function. For example, the inspiratory pressure may thus also represent the cost function, whose value shall be minimized in order to minimize the invasiveness/stress/discomfort of the mechanical ventilation for the patient, for example, when selecting the inspiration time and the inspiratory pressure as the first and second operating parameters. The course of the cost function, namely, the inspiratory pressure obtained at a defined value for the inspiration time when a target value is taken into account, can then the plotted over the inspiration time, and a line is obtained, which represents the value of the cost function. The selected operating parameter pair now lies on this line, preferably where the course of the line has a minimum.

As an alternative to this, the diagram may also be formed such that an interval of the values of the cost function is plotted in the diagram along a third axis extending at right angles to the first and second axes and that the value of the cost function is plotted along the third axis over each permissible operating parameter pair falling in the interval of the first axis and in the interval of the second axis. It is consequently also conceivable that a three-dimensional diagram is selected for the operating parameters and the values of the cost function calculated by the computer in order to display the course of the cost function for the user.

Finally, a plurality of lines may be formed in the diagram, and a value for the cost function is assigned to each line, and wherein the value of the cost function assigned to the line was calculated for the operating parameter pairs located on one of the lines. It is consequently also possible to select a contour line diagram for the course of the cost function.

A changed limit value is preset in another preferred embodiment of the method according to the present invention, the changed limit value being located between a range of allowed second ventilation parameter values and a range of non-allowed second ventilation parameter values. A second set of operating parameter limit value pairs is calculated from this by the computer from a first operating parameter value and a second operating parameter value, and the operating parameter limit value pairs of the second set are located between a first changed range of operating parameter pairs and a second changed range of operating parameter pairs, so that allowed second ventilation parameter values are obtained when setting operating parameter pairs from the first changed range and so that non-allowed second ventilation parameter values are obtained when setting operating parameter pairs from the second changed range, wherein the second set of operating parameter limit value pairs is displayed at positions corresponding to the values of the first and second operating parameters in the diagram.

By calculating second operating parameter limit value pairs from a changed limit value for a second ventilation parameter, the user can check what effect the change in a limit value has on the range of operating parameter pairs, which will then become available or will not become available any more.

Finally, in a preferred embodiment the target value range may be changed, wherein the above steps a) through e) are carried out with the changed target value range after changing the target value range, and a second target value is used to calculate permissible changed operating parameter values, and wherein the selected first operating parameter value and the changed selected first operating parameter value are outputted.

Similarly to the changing of the limit value for the second operating parameter, the target value range can thus also be varied in order to graphically display the changes resulting therefrom to a user.

According to another aspect of the present invention, the above object is accomplished, in addition, by a method for selecting the setting of at least one first operating parameter of a ventilation system, wherein the ventilation system has devices for feeding and removing breathing air to and from a patient, a display device with a screen and a computer and wherein the method has the following steps:
a) presetting a first target value range for a first ventilation parameter;
b) calculating permissible first operating parameter values by the computer for the at least one operating parameter, so that when a permissible first operating parameter value is set, the first ventilation parameter value is within the target value range;
c) presetting a limit value for a second ventilation parameter, wherein the limit value is between a range of allowed second ventilation parameter values and a range of non-allowed second ventilation parameter values;
d) calculating one or more first operating parameter limit values by the computer, wherein the operating parameter limit values are between a first range of first operating parameter values and a second range of first operating parameter values,
so that allowed second ventilation parameter values are obtained when setting first operating parameter values, and
so that non-allowed ventilation parameter values are obtained when setting first operating parameter values from the second range, and
e) outputting of the permissible first operating parameter values, which are within the first range, on the display device.

A target value range or, as was already described, only a single target value is preset at first for a first ventilation parameter, such as the respiratory minute volume, according to this aspect of the present invention. The computer subsequently calculates the permissible first operating parameter values that can be set on the ventilation system, so that then, when a permissible first operating parameter value, such as a permissible inspiration time value, is set on the ventilation system, the first ventilation parameter value that will now be obtained, i.e., for example, the respiratory minute volume, will be within the target value range.

In addition, a limit value, which makes a separation between a range of allowed second ventilation parameter values and a range of non-allowed second ventilation parameter values, is preset for a second ventilation parameter, for example, the tidal volume. The limit value consequently indicates the value for the second ventilation parameter, which should not be exceeded or dropped below.

Based on this, the computer calculates one or more operating parameter limit values, which separate a first range and a second range of operating parameter values from one another, wherein allowed second ventilation parameter values are obtained when setting values from the first range, while the setting of first operating parameter values from the second range on the ventilation system leads to non-allowed second ventilation parameter values.

Finally, the permissible first operating parameter values, which are in the first range, are displayed on the display device. This means that a user finds a display on the display device of the first operating parameter values for the ventilation system whose setting causes the first ventilation parameter value to be within the target value range, on the one hand, and at which, on the other hand, the limit for the second ventilation parameter is not exceeded or dropped below, depending on whether the limit value is an upper or a lower limit.

In a preferred embodiment of this method, the settings of a first operating parameter and of a second operating parameter are selected,
wherein permissible operating parameter value pairs are calculated by the computer in step b) for the first operating parameter and for the second operating parameter, so that when setting a permissible operating parameter value pair, the first ventilation parameter value is within the target value range,
wherein a set of operating parameter limit value pairs is calculated by the computer in step d) from a first operating parameter value and a second operating parameter value, wherein the operating parameter limit value pairs are between a first range of operating parameter pairs and a second range of operating parameter pairs, so that allowed second ventilation parameter values are obtained when setting operating parameter pairs from the first range, and so that non-allowed ventilation parameter values are obtained when setting operating parameter pairs from the second range,
wherein a diagram is generated by the display device on the screen,
in which diagram an interval of the first operating parameter is plotted along a first axis, wherein the interval is selected such that at least some of the permissible first operating parameter values are within the interval,
in which diagram an interval of the second operating parameter is plotted along a second axis, which extends at right angles to the first axis, wherein the interval is selected such that at least some of the permissible second operating parameter values are within the interval,
in which diagram the permissible operating parameter pairs from the first range corresponding to the values of the first operating parameter and of the second operating parameter are displayed in the diagram, and in which diagram the set of operating parameter limit value pairs is displayed at positions corresponding to the values of the first operating parameter and second operating parameter in the diagram.

Two operating parameters of the ventilation system, i.e., for example, the inspiration time and the inspiratory pressure, are set by the user in this embodiment of the method, and the pairs of first and second operating parameter values, whose setting leads, on the one hand, to a first ventilation parameter value, i.e., for example, a value for the respiratory minute volume, which value is in the target value range, and whose setting causes, on the other hand, the limit value for the second ventilation parameter, such as the tidal volume, not to be exceeded or dropped below, are displayed by the method according to the present invention in a two-dimensional diagram. This facilitates the selection of the operating parameters for the user.

In another preferred manner, a changed limit value can be preset in the method according to the present invention for the second ventilation parameter, the changed limit value being located between a range of allowed second ventilation parameter values and a range of non-allowed second ventilation parameter values, wherein a second set of operating parameter limit value pairs is calculated by the computer from a first operating parameter value and a second operating parameter value, wherein the operating parameter limit value pairs of the second set are located between a first changed range of operating parameter pairs and a second changed range of operating parameter pairs, so that allowed second ventilation parameter values are obtained when setting operating parameter pairs from the first changed range and so that non-allowed second ventilation parameter values are obtained when setting operating parameter pairs from the second changed range, and wherein the second set of operating parameter limit value pairs is displayed in the diagram at positions corresponding to the values of the first and second operating parameters.

A user can have the effects, which arise when a limit value for the second ventilation parameter is varied, displayed in a simple manner in this embodiment.

The present invention will be described below in drawings showing only preferred exemplary embodiments. The present invention is described in detail below with reference to the attached figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
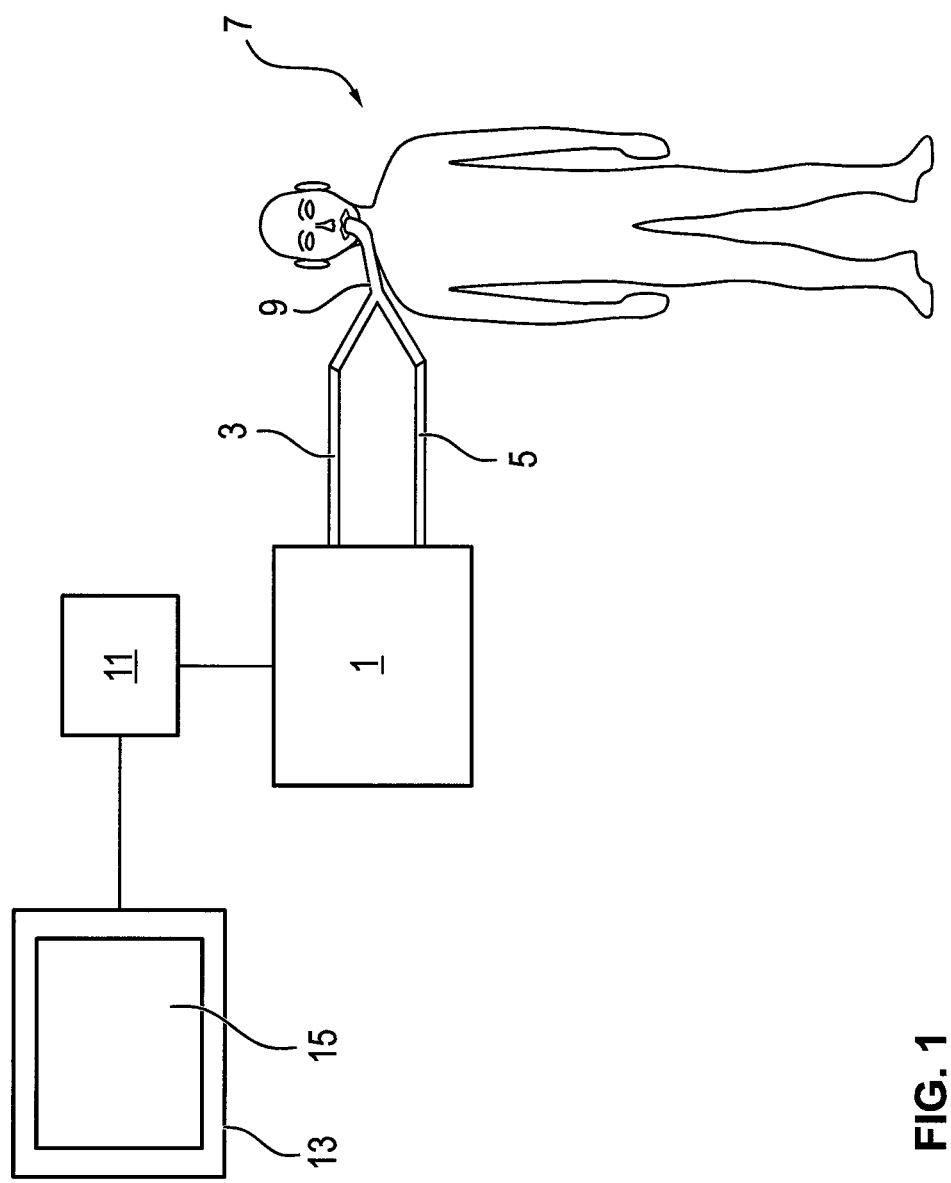
FIG. 1 is a schematic view of a ventilation system, with which the exemplary embodiments of the method according to the present invention can be carried out.

Referring to the drawings, FIG. 1 shows a schematic view of a ventilation system, which has a ventilator device 1, with which breathing air is fed to or removed from a patient 7 via a first line 3 and a second line 5. A Y-piece 9, via which the patient 7 is connected to the two lines 3, 5, is provided for this at the end of the first and second lines 3, 5, which end points to the patient 7. The device 1 is connected via a computer 11 to a display device 13, on which a screen 15 is, in turn, provided. The display device 13 includes a setting device.

The first exemplary embodiment of the method according to the present invention will now be explained on the basis of FIGS. 2 through 5, which describes the procedure followed to select a first operating parameter and a second operating parameter of the ventilation system and especially of the ventilation device 1 for feeding and removing the breathing air. The first operating parameter in this exemplary embodiment is the inspiration time $T_{insp}$ and the second operating parameter is the inspiratory pressure $P_{insp}$.

A first target value range is entered on a corresponding inputting device such as softkeys displayed on the screen or a mechanical input interface (the software based input (softkey) and the mechanical input may be buttons, wheels, sliders, keys and other known input features) on the display ventilation device 13. The first target value range that is entered is selected first by the user for a first ventilation parameter in the first exemplary embodiment of a method according to the present invention. In the preferred exemplary embodiment described here, this first ventilation parameter is the respiratory minute volume, i.e., the breathing air volume sent to the patient 7 per minute, and a value range, in which this ventilation parameter shall be during the ventilation of the patient, is preset by the target value range. A user enters an upper limit and a lower limit, to define the target value range.

If, however, the upper limit and the lower limit are selected such that they are identical, as this happens in this exemplary embodiment, the target value range is reduced to a single value, which shall, however, also be covered by the term "target value range" in the sense of the present invention.

On the basis of a model, the computer 11 calculates, in a manner known per se, permissible operating parameter pairs for the first operating parameter and the second operating parameter, namely, the inspiration time and the inspiratory pressure, by means of patient parameters, so that the first ventilation parameter value is within the target value range, i.e., the target value is reached in this case, if a permissible operating parameter pair is set. These permissible operating parameter pairs are located on a line.

This calculation of the permissible operating parameter values as well as of other values mentioned below can be performed on the basis of the principles described in C. Schranz, T. Becher, D. Schädler, N. Weiler, K. Möller, "Model-based setting of inspiratory pressure and respiratory rate in pressure-controlled ventilation," Physiol. Meas., 2014, Vol. 35(3), pp. 383-397, which is incorporated herein by reference. It is, however, also possible to use other mathematical models for the permissible operating parameter pairs calculation.

The computer 11 then calculates the values of a preset cost (invasiveness/stress/discomfort) function on the basis of the target value, or possibly of a target value from the target value range, the cost function being a function of at least one operating parameter, i.e., of the inspiratory pressure. The value of the of a preset cost function is an indicator of how high the stress or invasiveness or discomfort is for the patient when the respective first operating parameter and ventilation parameter is set, so that, for example, a lower value for the cost function represents a lower stress for the patient In this preferred exemplary embodiment, the value of the cost function is the value of the inspiratory pressure $P_{insp}$, which is obtained on the basis of a lung model, if the respiratory minute volume is preset as a target value and the inspiration time $T_{insp}$ is varied.

Figure 2:
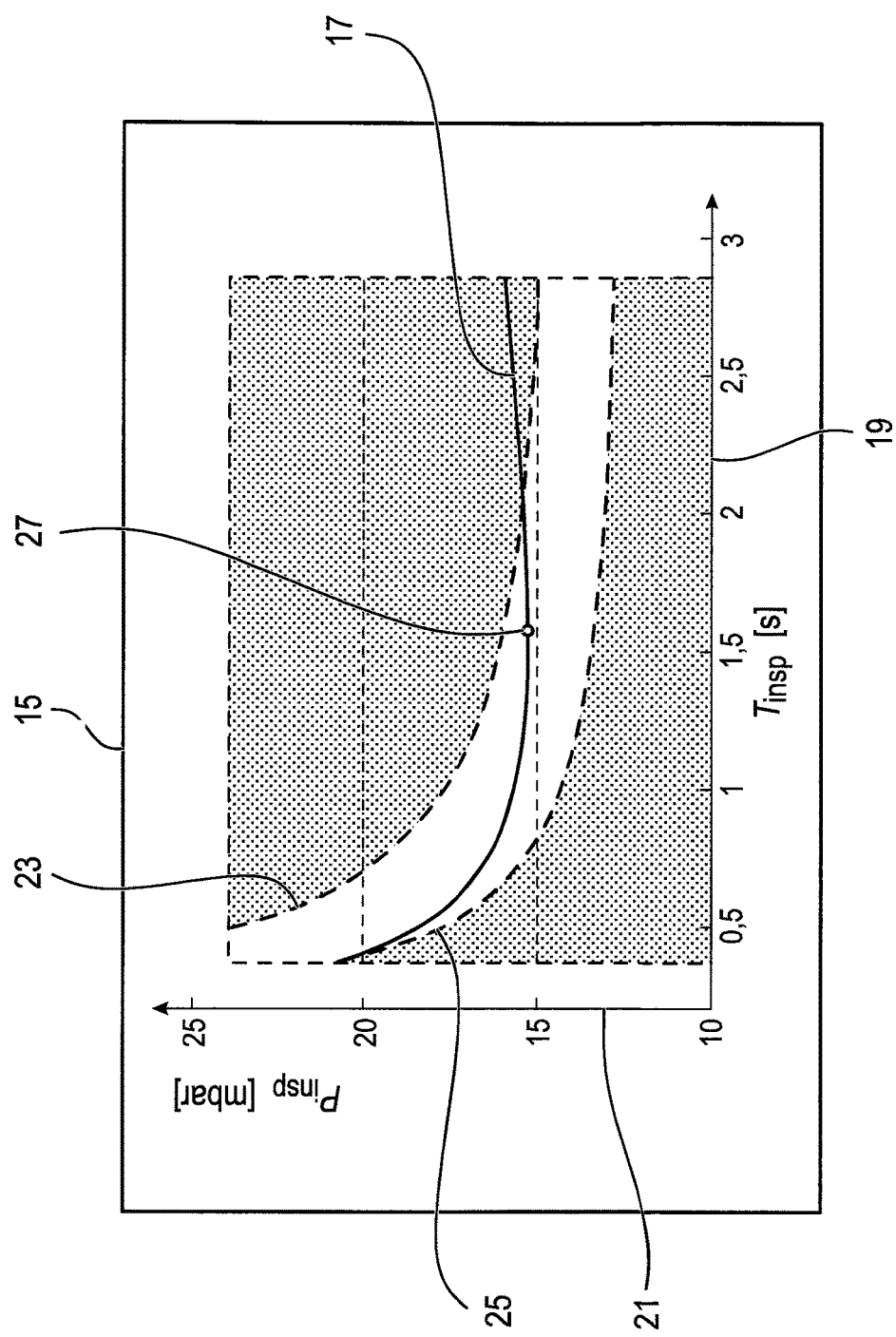
FIG. 2 is a first view of the display device of the ventilation system from FIG. 1 when carrying out a first exemplary embodiment of a method according to the present invention.

The calculated permissible operating parameter pairs 17 are displayed as a line or target ventilation curve in the view of the screen 15 of the display ventilation device 13, which view is shown in FIG. 2, the first operating parameter Tinsp being plotted along a first axis 19, while the second operating parameter Pinsp is plotted along a second axis 21 extending at right angles to the first axis 19. The target ventilation curve corresponds to the target value as explained in the previous paragraph.

The value ranges along the first and second axes 19, 21 are selected here as follows. An interval of the first operating parameter $T_{insp}$ is plotted along the first axis 19, and this interval is selected such that at least some of the permissible first operating parameter values are within the interval. Likewise, an interval of the second operating parameter $P_{insp}$ is plotted along the second axis 21, and this interval is selected such that at least some of the permissible second operating parameters values are within the interval. It is thus ensured that the diagram shows at least parts of the permissible operating parameter pairs.

In addition to the permissible operating parameter pairs 17, a first set of operating parameter limit value pairs 23 is also displayed in the diagram generated on the screen 15 according to FIG. 2, and this set likewise forms a line or upper limit ventilation curve. This set of operating parameter limit value pairs or curve 23 is likewise calculated by the computer 11, and the set of operating parameter limit value pairs 23 is obtained from a limit value preset by the user for a second ventilation parameter, here the tidal volume, i.e., the respiratory minute volume fed to the patient 7 per breath.

The operating parameter limit value pairs, which form the set or curve 23, are value pairs from the first operating parameter $T_{insp}$ and the second operating parameter $P_{insp}$ at which this upper limit value for the tidal volume is just reached. This set 23 of operating parameter limit value pairs thus yields precisely a boundary line between allowed operating parameters (light area, allowable operating region) and non-allowed operating parameters (gray-shaded area).

In addition to the first set of operating parameter limit value pairs 23, the diagram in FIG. 2 also displays another set of operating parameter limit value pairs 25, which is obtained from a lower limit value for the tidal volume. Another boundary line or lower limit ventilation curve, which further defines the range of the allowed operating parameters, is thus generated by this additional set of operating parameter limit value pairs 25.

Finally, the computer 11 selects an operating parameter pair 27 from values for the first and second operating parameters $T_{insp}$, $P_{insp}$, at which pair 27 the cost function, which coincides with the second operating parameter, i.e., the inspiratory pressure, in this exemplary embodiment, has a minimum, and this selected operating parameter pair 27 is located within the allowed range of operating parameters. The selected operating parameter pair 27 thus corresponds to the point at which the cost function and hence the inspiratory pressure $P_{insp}$ has an optimum, and is minimal here, on the one hand, and the respiratory minute volume preset as a first target value is nevertheless reached.

When the user would like to use this selected operating parameter pair 27 from the first and second operating parameters $T_{insp}$, $P_{insp}$, the user must confirm this by actuating a confirmation key or enter these values in another manner, and the ventilation device 1 will then be operated with these operating parameter values. As an alternative, the selected operating parameters may be automatically transmitted to the device.

Figure 3:
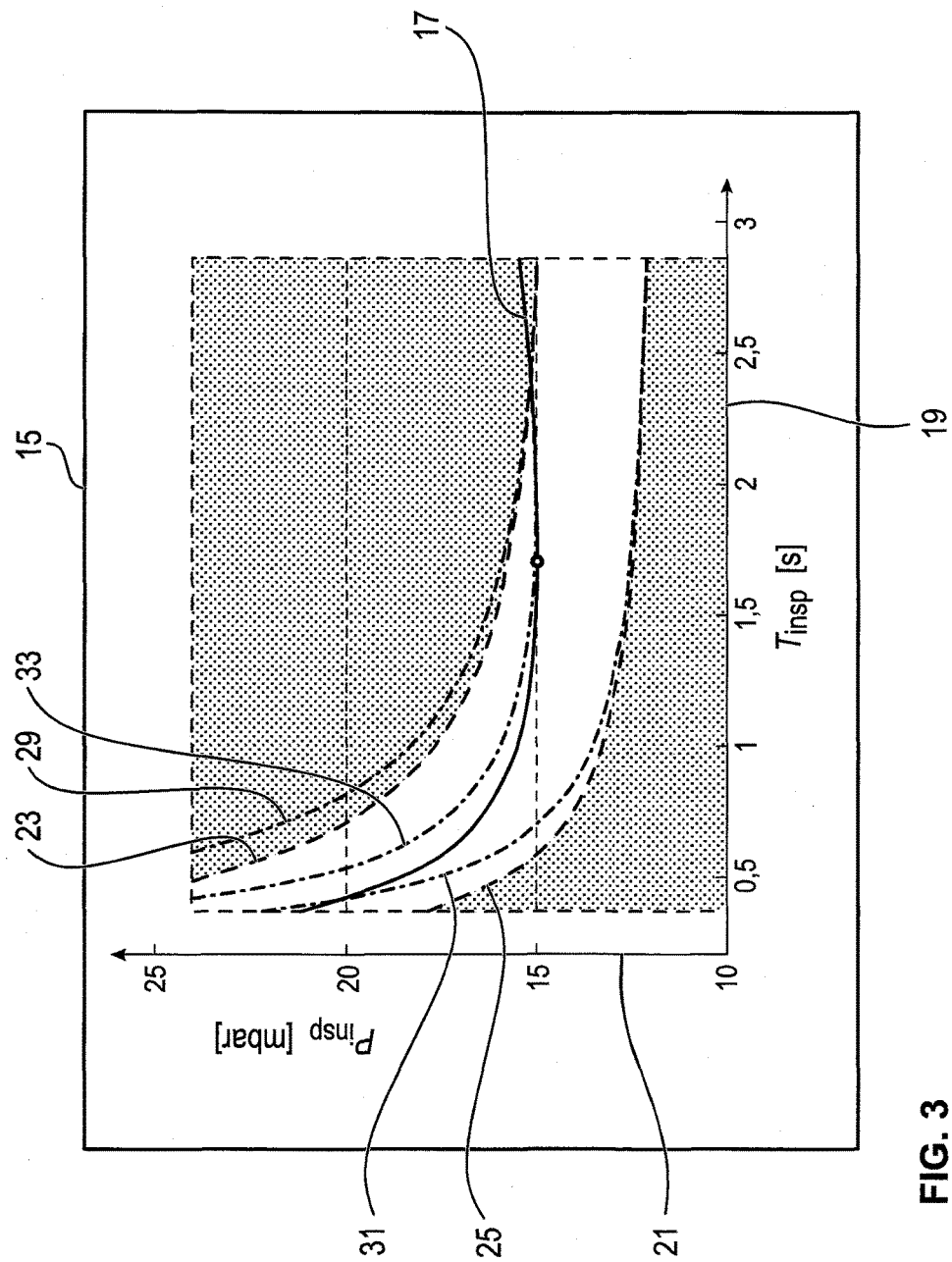
FIG. 3 is a second view of the display device of the ventilation system from FIG. 1.

In addition to the first set of operating parameter limit value pairs 23, a second set of operating parameter limit value pairs 29 is also displayed in the diagram, which is shown in FIG. 3 and is shown on the screen 15 of the display ventilation device 13, according to another possibility of the first exemplary embodiment of the method according to the present invention, and this second set 29 is obtained by a changed limit value having been preset by the user for the second ventilation parameter, i.e., the tidal volume, and having used as the basis of the calculation by the computer 11, said limit value being slightly increased compared to the first limit value, from which the first set of parameter limit value pairs 23 results. The changed limit value is between a range of allowed second ventilation parameter values and a range of non-allowed second ventilation parameter values, and the operating parameter limit value pairs of the second set 29 are now between a first changed range of operating parameter pairs and a second changed range of operating parameter pairs, so that allowed second ventilation parameter values are obtained when setting operating parameter pairs from the first changed range and non-allowed second ventilation parameter values are obtained when setting operating parameter pairs from the second changed range. An additional set of operating parameter limit value pairs 31 resulting from a changed lower limit value is analogously given.

These additional changed limit values were entered before on the display ventilation device 13 by the user, and the exemplary embodiment of the method according to the present invention makes it possible to display the change in the position of the boundary line between allowed and non-allowed operating parameter combinations.

A user may analogously also select a changed target value range or target value for the respiratory minute volume, and the computer 11 recalculates the permissible operating parameter pairs 33. A user can thus also assess the change in the course of the permissible operating parameter pairs 17, 33 and the change associated herewith in the selected optical operating parameter pair.

Figure 4:
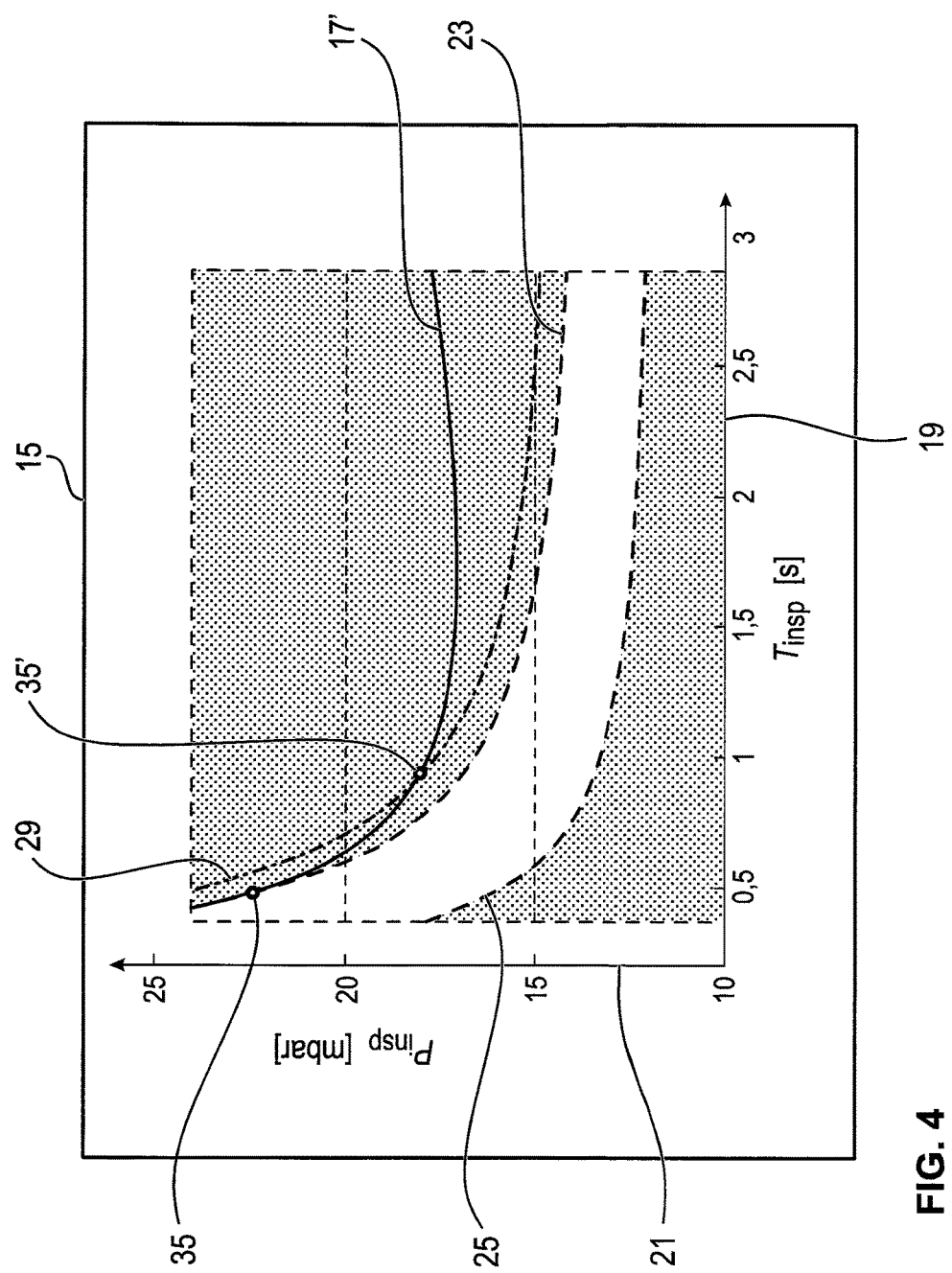
FIG. 4 is a third view of the display device of the ventilation system from FIG. 1.

Another aspect of the first exemplary embodiment of the method according to the present invention is shown in the diagram shown in FIG. 4 and on the screen 15 of the ventilation system.

A first set and a second set of operating parameter limit value pairs 23, 25, which separate an allowed range from a non-allowed range of operating parameter pairs, were calculated by the computer 11 in this case as well. The sets 23, 25 are based, in turn, on the limit values for the tidal volume, which were already discussed in connection with FIG. 2 and with which the operating parameter limit value pairs of the sets 23, 25 were calculated.

Moreover, FIG. 4 shows second permissible operating parameter pairs 17' calculated on the basis of a target value for the respiratory minute volume, which target value was changed compared to the diagram shown in FIGS. 2 and 3. Furthermore, a second set of operating parameter limit value pairs 29 was calculated, which is obtained from a slight increase in the limit value for the tidal volume.

If the first set of operating parameter limit value pairs 23 is used, the computer 11 selects a first operating parameter pair 35, whose value for the cost function is comparatively high corresponding to an inspiratory pressure $P_{insp}$. If, however, the second set of operating parameter limit value pairs 29 is used as the basis, the computer 11 selects a second operating parameter pair 35', for which the inspiratory pressure $P_{insp}$ and hence also the invasiveness/stress/discomfort are markedly reduced.

By displaying the two sets 23, 25 for the different limit values, the user is thus enabled to check the effect a slight increase in the limit value has on the selected operating parameter pair 35, 35'. Such an increase would lead to a considerable reduction of the inspiratory pressure $P_{insp}$ used during the ventilation, and the invasiveness/stress/discomfort would be markedly reduced in the exemplary embodiment being shown here.

Figure 5:
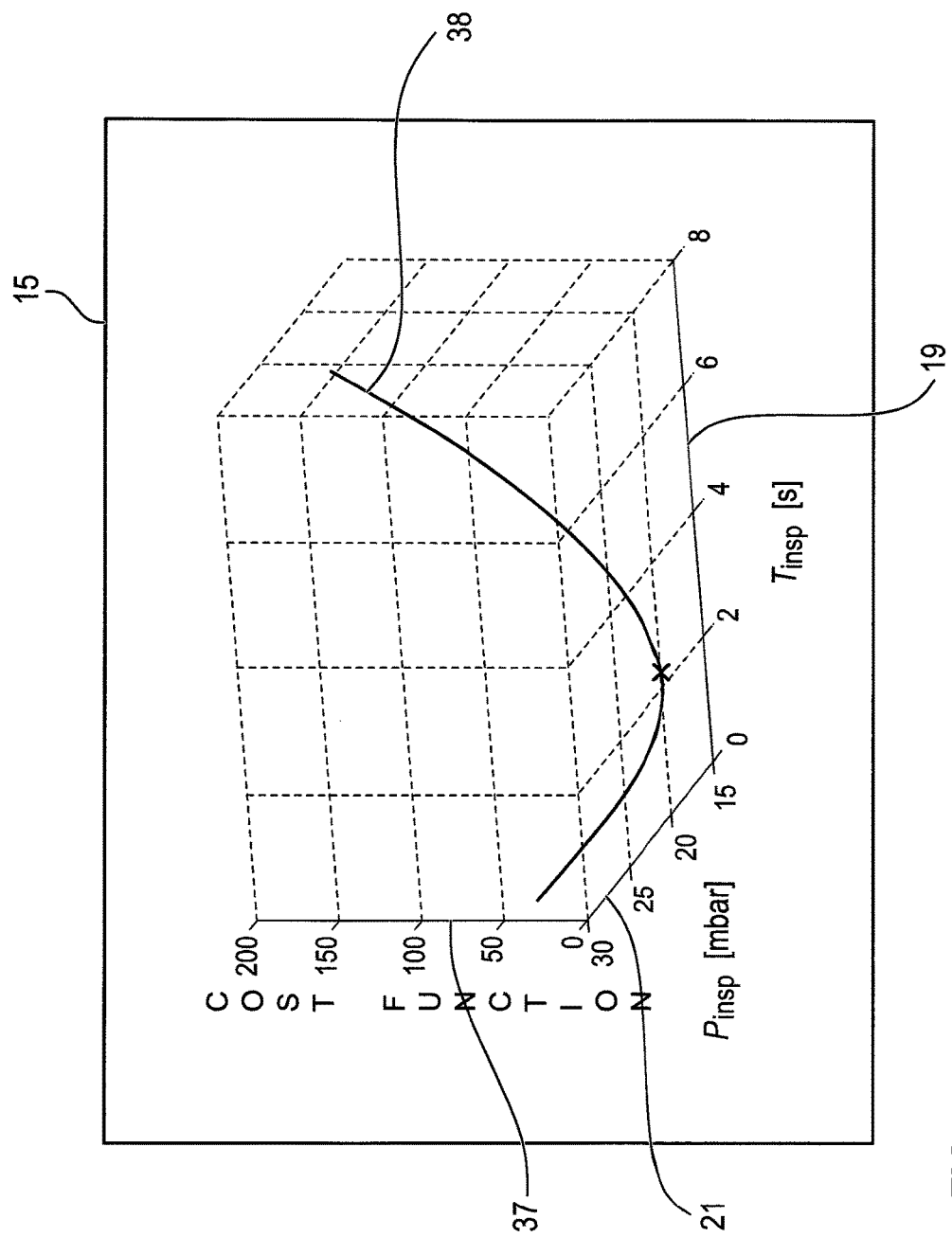
FIG. 5 is a fourth view of the display device of the ventilation system from FIG. 1.

FIG. 5 shows an alternative within the first exemplary embodiment, in which an interval of the values of the cost function is plotted in the diagram shown on the screen 15 along a third axis 37 extending at right angles to the first and second axes 19, 21, wherein the value of the cost function is plotted along the third axis 37 over each permissible operating parameter pair falling in the interval of the first axis 19 and in the interval of the second axis 21.

Since the target value range was limited to a single target value for the first ventilation parameter in this case, the range of the permissible operating parameter pairs is a line, so that the points of the values of the cost function 38 merely form a line in this diagram.

If, however, the target value range extends between upper and lower limits, which are different from each other, the range of permissible operating parameter pairs is, as a rule, also no longer linear, but it forms an area, and the cost function is likewise described by an area in a diagram similar to that shown in FIG. 5.

Figure 6:
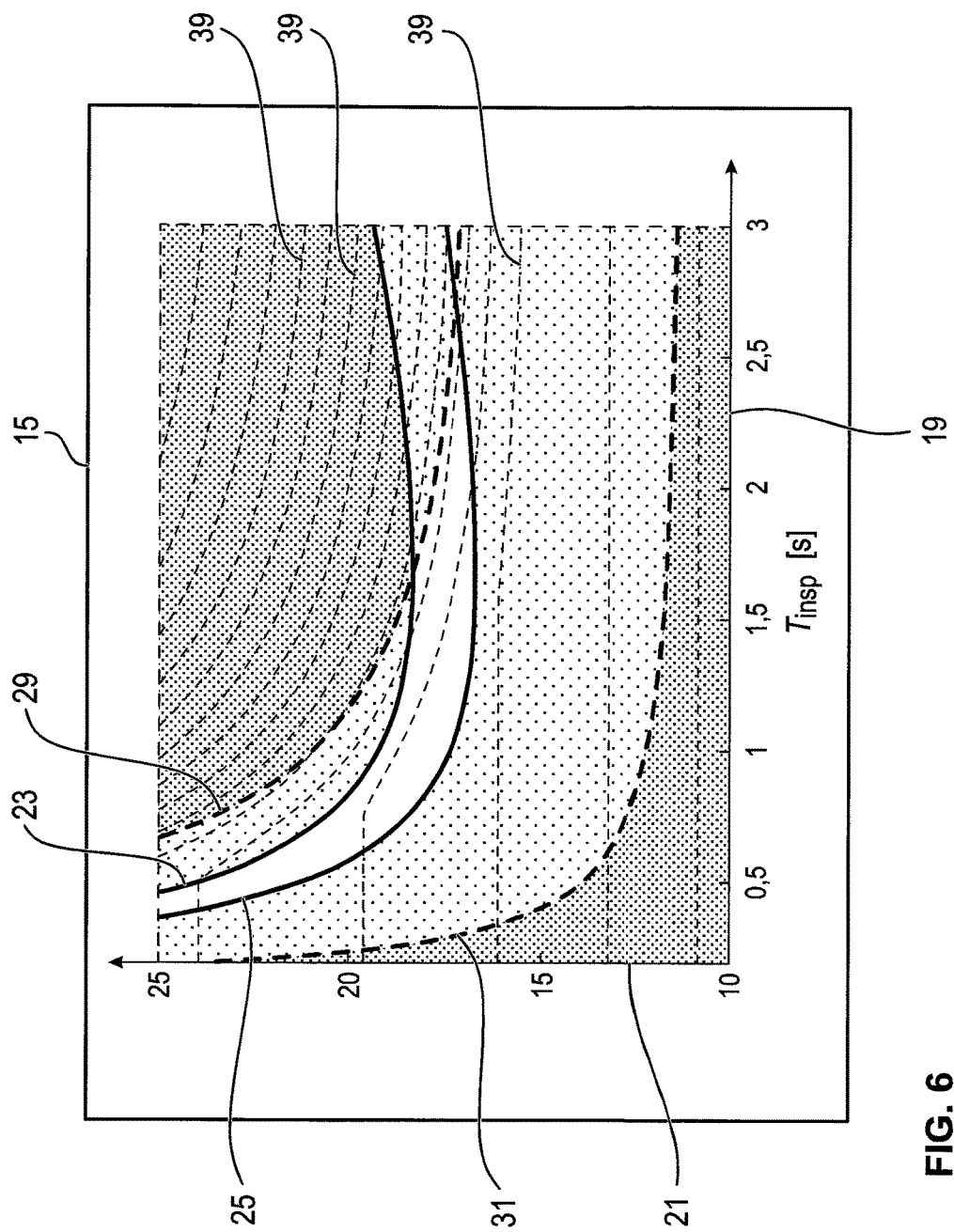
FIG. 6 is a fifth embodiment of the display device of the ventilation system from FIG. 1.

As an alternative to the diagram of the values of the cost function from FIG. 5, it is also possible to select a diagram with contour line, as it is done in FIG. 6.

This diagram shows, at first, first and second sets of operating parameter limit value pairs 23, 29 as well as additional sets of parameter limit value pairs 25, 31, which are obtained in the manner already described above from different limit values for the second ventilation parameter in the form of the tidal volume.

In addition, a plurality of lines 39 are formed in this diagram, and a value for the cost function is assigned to each line 39, and the value of the cost function, which value is assigned to the line, was calculated for the operating parameter pairs located on one of the lines 39. A contour line diagram was thus selected for the cost function, and the height can additionally be color-coded.

Figure 7:
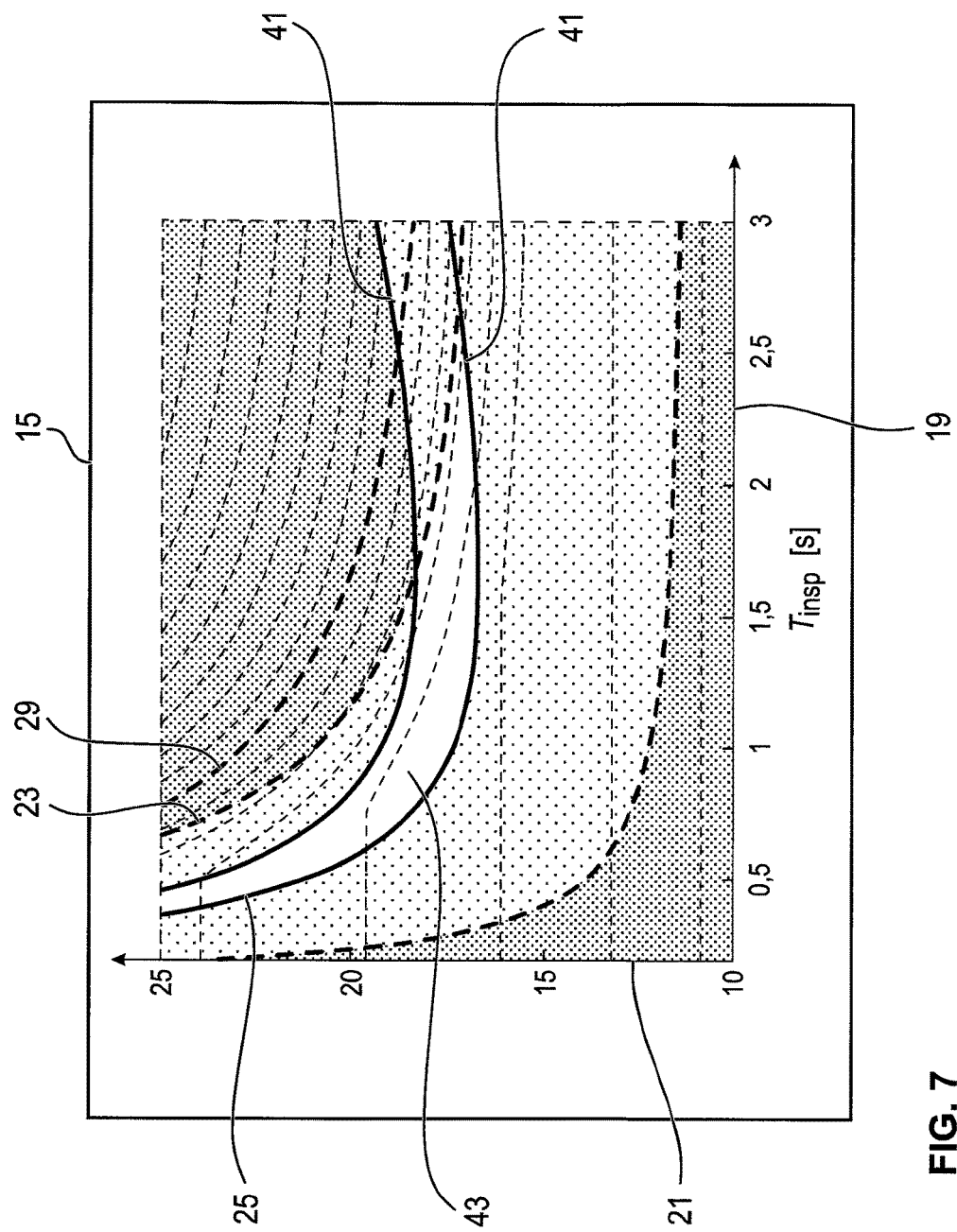
FIG. 7 is a sixth view of the display device of the ventilation system from FIG. 1 when carrying out a second exemplary embodiment of a method according to the present invention.

While the values of a cost function were calculated by the computer 11 in the exemplary embodiment of the method according to the present invention, which was explained in connection with FIGS. 2 through 6, this may also be omitted, as it will be explained below on the basis of the diagram shown on the screen 15 for a second exemplary embodiment of a method according to the present invention, which is shown in FIG. 7.

A first target value range, which is entered on a corresponding input device at the display ventilation device 13, is again preset by a user for a first ventilation parameter, such as the respiratory minute volume, in this second exemplary embodiment. The user sets an upper limit and a lower limit, so that the target value range is defined by these. The upper and lower limits may, however, also be selected such that they are identical, so that the target value range shall also be covered by the term "target value range" in the sense of the present invention.

The computer 11 subsequently calculates permissible operating parameter pairs for the first and second operating parameters from the inspiration time and inspiratory pressure in a manner known per se on the basis of a model with additional patient parameters, so that the first ventilation parameter value is within the target value range when setting a permissible operating parameter pair.

The first operating parameter $T_{insp}$ is plotted along a first axis 19 in the view of the screen 15 of a display ventilation device 13, which view is shown in FIG. 7, while the second operating parameter $P_{insp}$ is plotted along a second axis 21 extending at right angles to the first axis 19. The value ranges are selected along the first and second axes 19, 21 as follows. An interval of the first operating parameter $T_{insp}$ is plotted along the first axis 19, and this interval is again selected such that at least some of the permissible first operating parameter values are within the interval. Likewise, an interval of the second operating parameter $P_{insp}$ is plotted along the second axis 21, and this interval is selected such that at least some of the permissible second operating parameter values are within the interval. It is thus ensured that the diagram shows at least parts of the permissible operating parameter pairs. The range of the permissible operating parameter pairs is defined by boundary lines 41 in this diagram.

A first set of operating parameter limit value pairs 23 is also indicated in the diagram generated on the screen 15 according to FIG. 7, and this set also forms a line. This set of operating parameter limit value pairs 23 is calculated by the computer 11, and it is obtained from a limit value preset by the user for a second ventilation parameter, here the tidal volume, i.e., the breathing air volume fed to the patient 7 per breath.

The operating parameter limit value pairs forming the set 23 are thus such value pairs from the first operating parameter $T_{insp}$ and the second operating parameter $P_{insp}$ at which this upper limit value for the tidal volume is just reached. The set of operating parameter limit value pairs is therefore a boundary line between allowed operating parameters (light area) and non-allowed operating parameters (shaded area). The operating parameter limit value pairs are located between a first range of operating parameter pairs and a second range of operating parameter pairs, and allowed second ventilation parameter values are obtained when operating parameter pairs are set from the first range and non-allowed second ventilation parameter values are obtained when operating parameter pairs are set from the second range.

Yet another set of parameter limit value pairs 25, which is obtained from a lower limit value for the tidal volume, is displayed in the diagram from FIG. 7 in addition to the first set of operating parameter limit value pairs 23. An additional boundary line, which further defines the range of the allowed operating parameters, is thus generated by this additional set of operating parameter limit value pairs 25.

The allowed operating parameter pairs that are located, in addition, within the first range defined by the sets of operating parameter limit values 23, 25, whose setting on the ventilation device 1 consequently leads to allowed second ventilation parameter values, are outputted for a user in the diagram according to FIG. 7 by the range of these pairs being defined by the boundary lines 41, on the one hand, and by the sets of operating parameter limit value pairs 23, 25, on the other hand.

This means that this range coincides with the area 43 and is very easily recognizable for the user. The setting for the ventilation device 1 can be selected from this range.

As can be seen, in addition, in FIG. 7, a changed limit value can additionally be preset for the second ventilation parameter, and the changed limit value is likewise between a range of allowed second ventilation parameter pairs and a range of non-allowed second ventilation parameter pairs.

A second set of operating parameter limit value pairs 29 is calculated from this by the computer 11 from a first operating parameter value and a second operating parameter value, and the operating parameter limit value pairs of the second set 29 are located between a first changed range of operating parameter pairs and a second changed range of operating parameter pairs, so that allowed second ventilation parameter values are obtained when operating parameter pairs are set from the first changed range and so that non-allowed second ventilation parameter values are obtained when setting operating parameter pairs from the second changed range. The second set of operating parameter limit value pairs 29 is displayed in the diagram at positions corresponding to the values of the first and second operating parameters, so that it is visualized for a user how a change in a limit value for the second ventilation parameter affects the position of the area 43.

Figure 8:
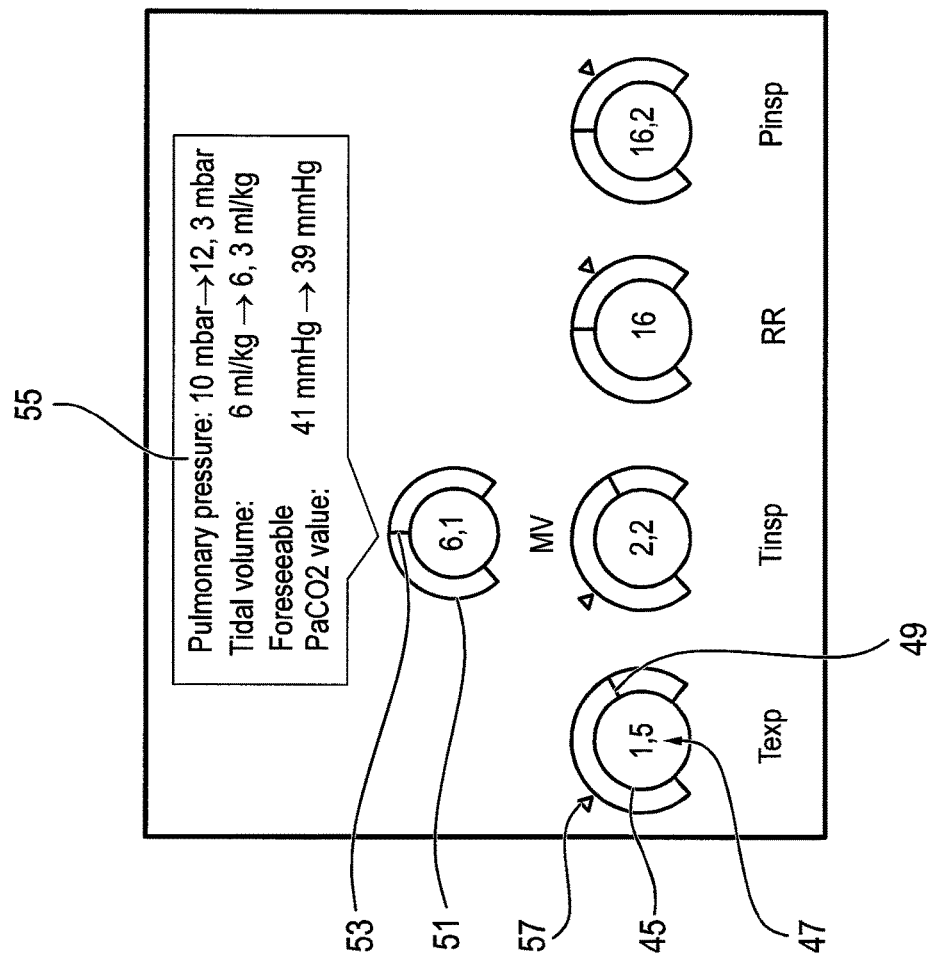
FIG. 8 is an additional view of the display device of the ventilation system from FIG. 1.

In addition to the diagrams on the screen 15 of the display ventilation device 13, which are shown in FIGS. 2 through 7, the diagram shown in FIG. 8 may also be displayed on the screen 15 in the first and second exemplary embodiments of the method.

Circular diagrams 45 with numerical value 47 for the individual operating parameters, such as expiration time $T_{exp}$, inspiration time $T_{insp}$, etc., are displayed, and the angular position of a dash or line 49 in the circle or arc portion 45 corresponds to the operating parameter just set.

There is a circular diagram 51 for the target value in the upper area of the diagram, and the angular position of a dash 53 likewise corresponds in this case to the value actually set for the target value, i.e., to the respiratory minute volume. Above the circle or arc portion 51 for the target value is arranged a window 55, in which the values that are obtained when the respiratory minute volume or the target value changes are indicated. Arrows 57 corresponding to the changed values are correspondingly displayed in the diagrams in the lower area for the individual operating parameters.

Figure 9:
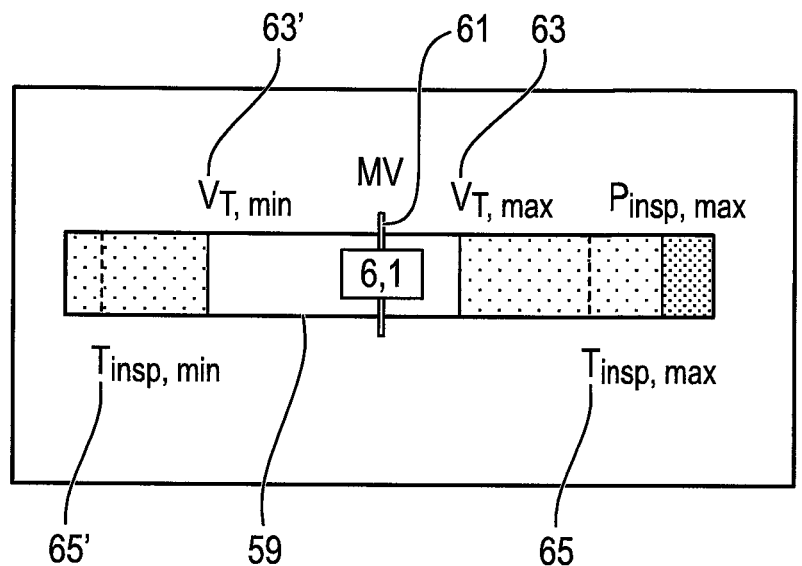
FIG. 9 is a view of the display device which is obtained in a third exemplary embodiment of the method according to the present invention.
Figure 10:
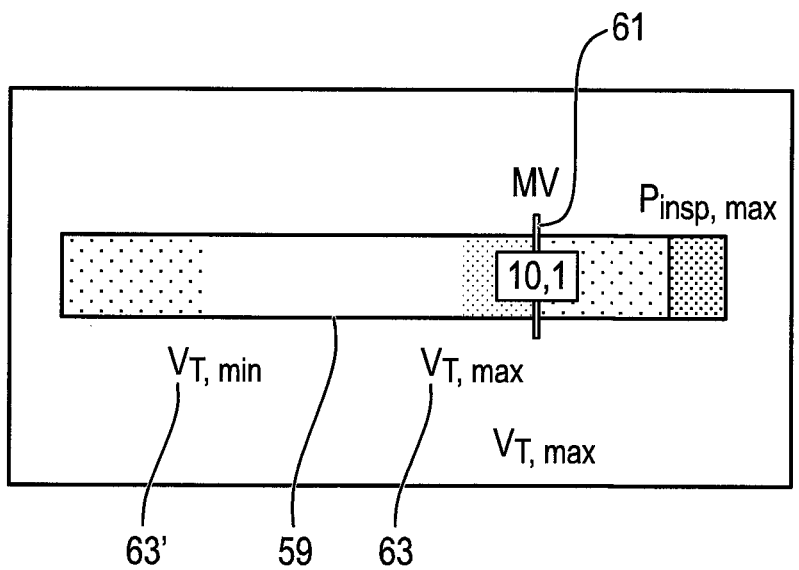
FIG. 10 is another view of the display device which is obtained in a third exemplary embodiment of the method according to the present invention.

FIGS. 9 and 10 show the diagram displayed on the screen 15 of the display ventilation device 13, which diagram is obtained in a third exemplary embodiment of the method according to the present invention.

A first target value range or, as here, a single first target value is preset in this case for the respiratory minute volume. The computer 11 now calculates permissible operating parameter values for at least one first operating parameter, namely, the inspiration time, on the basis of a model in a manner that is known per se, so that when a permissible operating parameter value is set, the first ventilation parameter is within the target value range, i.e., the target value is consequently reached in this case.

The values of a preset cost function, which is a function of at least the first operating parameter, are subsequently calculated by the computer 11 in this case as well.

In addition, a first operating parameter limit value is calculated by the computer 11 for the at least one operating parameter, the first operating parameter limit value being a function of a preset first limit value for a second ventilation parameter, such as the tidal volume. This first limit value is preset by the user. The first operating parameter limit value is located between a first range of first operating parameter values and a second range of first operating parameter values, so that allowed second ventilation parameter values are obtained if first operating parameter values are set from the first range and non-allowed second ventilation parameter values are obtained when setting first operating parameter values from the second range.

Finally, the computer 11 selects a first, preferably permissible operating parameter value, at which the value of the cost function has an optimum, the selected first operating parameter value being selected from first operating parameter values from the first range.

The diagram shown in FIG. 9 is then generated on the screen 15 in such a way that an interval of the first ventilation parameter, i.e., a range for the respiratory minute volume, is plotted parallel to the first axis 19 and the target value 53 and a first ventilation parameter limit value 55, resulting from the first limit value, is plotted parallel to the first axis 19, the first ventilation parameter limit value forming a boundary between values allowed and values not allowed for setting the target value 53.

An interval of the first ventilation parameter, i.e., of the respiratory minute volume, is plotted along a line 59, and said interval is selected to be such that it at least overlaps with the target value range. The diagram shows a marker 61 at a position along line 59, which corresponds to the position in the interval.

In addition, the first ventilation parameter value obtained when setting the first operating parameter limit value is calculated by the computer 11 with the first operating parameter limit value, and a limit value marker 63 is additionally provided in the diagram along the line 59, and the position of the limit value marker 63 along the line 59 corresponds to the calculated first ventilation parameter value. An additional limit value marker 63' is generated along the line 59 in the same manner for a second limit value of the second ventilation parameter.

In addition, a first operating parameter limit and a second operating parameter limit are preset for the first operating parameter, and parameter limit markers 65, 65' are generated along the line 59 in the diagram, the position of these markers 65, 65' along the line 59 being calculated by the computer such that the position corresponds to the first ventilation parameter value that is obtained when the operating parameter limits are set as a first operating parameter.

The marker 61 can be displaced along the line 59 by means of a setting device, which is provided at the display device 15 and is preferably designed as a setting wheel, and a changed target value is selected hereby. This procedure is shown by a comparison of FIGS. 9 and 10, from which it can be seen that the marker 61 was displaced and the target value was changed as a result. After displacing the marker 61, the computer 11 calculates the changed first operating parameter value with which the changed target value is obtained and the changed first operating parameter value is set. It is necessary in this connection for an optimum to be again selected from the values of the cost function.

If the displacement of the marker 61 and the change in the target value for the first ventilation parameter, i.e., the respiratory minute volume, which change is associated therewith, leads to the case in which the second ventilation parameter value calculated in this case with changed first operating parameter value is a non-allowed second ventilation parameter, the limit value is set at the calculated second ventilation parameter, and the first operating parameter limit value is set at the changed first operating parameter value.

This is likewise shown in the diagram in FIG. 10. The marker 61 has been moved to the right beyond the limit value marker 63, the consequence of which was that the limit value of the second ventilation parameter, namely, the tidal volume, was exceeded. The value for the tidal volume, which was obtained with the selected new setting of the respiratory minute volume, was then taken over as a changed limit value. In addition, the operating parameter limit value is set at the first operating parameter value, which was calculated before by the computer 11 with the target value.

It appears from the description of the exemplary embodiments of the method according to the present invention that the selection of the operating parameters is markedly simplified for a user by means of the present invention because the effects of the change of target values can be immediately illustrated, so that a user can qualitatively readily assess the effect of the change in the target value. In addition, the present invention makes it possible to adapt limit values such that the stress (and/or invasiveness and/or discomfort) for a patient can possibly be significantly reduced, because the value of the cost function, which value is obtained from the selected operating parameters, can now be markedly reduced.

While specific embodiments of the invention have been shown and described in detail to illustrate the application of the principles of the invention, it will be understood that the invention may be embodied otherwise without departing from such principles.

LIST OF REFERENCE NUMBERS

1 Device for feeding and removing
3 First line
5 Second line
7 Patient
9 Y-piece
11 Computer
13 Display device
15 Screen
17 Permissible operating parameter pairs
19 First axis
21 Second axis
23 First set of operating parameter limit value pairs
25 Additional set of operating parameter limit value pairs
27 Selected combination
29 Second set of operating parameter limit value pairs
31 Additional set of operating parameter limit value pairs
33 Permissible operating parameter pairs
35' First selected combination
37 Value of the cost function for all permissible operating parameter pairs
39 Lines
41 Boundary lines
43 Area
45 Circle
47 Value
49 Dash
51 Circle
53 Dash
55 Window
57 Arrow
59 Line
61 Marker
63, 63' Limit value marker
65. 65' Parameter limit marker

What is claimed is:

1. A method for selecting a setting of at least one first operating parameter of a ventilation system comprising devices for feeding breathing air to a patient and removing breathing air from the patient, a computer and a display device with a screen, the method comprising the steps of:
presetting a first target value range for a first ventilation parameter;
calculating a plurality of permissible first operating parameter values, by the computer, for the first operating parameter, such that the first ventilation parameter value is within the target value range for the first ventilation parameter when the permissible first operating parameter value is set, the first operating parameter being different than the first ventilation parameter;
calculating the values of a preset cost function, by the computer, which preset cost function is a function of at least one operating parameter;
selecting a first operating parameter value at which the value of the cost function has an optimum, by the computer;
outputting the selected first operating parameter value on the screen of the display device; and
ventilating the patient as a function of the selected first operating parameter value.

2. A method in accordance with claim 1, further comprising:
presetting a limit value for a second ventilation parameter, wherein the limit value for the second ventilation parameter is located between a range of allowed second ventilation parameter values and a range of non-allowed second ventilation parameter values;
calculating the operating parameter limit value or more first operating parameter limit values by the computer, wherein the first operating parameter limit values are located between a first range of first operating parameter values and a second range of first operating parameter values;
obtaining allowed second ventilation parameter values when first operating parameter values are set from the first range;
obtaining non-allowed second ventilation parameter values when first operating parameter values are set from the second range; and
selecting the selected first operating parameter value from first operating parameter values from the first range in the step of selecting a first operating parameter value at which the value of the cost function has an optimum.

3. A method in accordance with claim 2, wherein:
the computer calculates, after displacement of the marker, the changed first operating parameter value with which the changed target value is obtained;
the changed first operating parameter value is set;
the limit value is set at the second ventilation parameter; and
the first operating parameter limit value is set at the changed first operating parameter value if the second ventilation parameter value calculated with the changed first operating parameter value is one of the non-allowed second ventilation parameter.

4. A method in accordance with claim 1, wherein:
a diagram, in which an interval of the first ventilation parameter is plotted along a line, is generated on the screen of the display device;
the interval is selected such that the interval at least overlaps with the target value range; and
the diagram has a marker at a position along the line, which marker corresponds to the target value.

5. A method in accordance with claim 2, wherein:
the computer calculates with a first operating parameter limit value the first ventilation parameter value obtained when the first operating parameter limit value is set; and
a limit value marker is provided along the line;
a position of the limit value marker along the line corresponds to the calculated first ventilation parameter value.

6. A method in accordance with claim 4, wherein:
at least one first operating parameter limit is preset for the first operating parameter;
a parameter limit marker has a parameter limit marker position along the line that is calculated by the computer such that the parameter limit marker position corresponds to the first ventilation parameter value, which is obtained when the operating parameter limit is set as the first operating parameter; and
parameter limit marker is provided along the line in the diagram that is generated on the screen of the display device.

7. A method in accordance with claim 4, wherein:
the ventilation system has a setting device, which is designed such that the marker can be displaced along the line by adjusting the setting device, and
a changed target value is selected by displacing the marker along the line.

8. A method in accordance with claim 7, wherein:
the computer calculates, after displacement of the marker, the changed first operating parameter value with which the changed target value is obtained; and
the changed first operating parameter value is set.

9. A method in accordance with claim 1, wherein:
settings of the first operating parameter and a second operating parameter are selected;
said step of calculating permissible first operating parameter values, by the computer for the first operating parameter, further comprises calculating permissible second operating parameter values by the computer so that the first ventilation parameter value is within the target value range if a permissible operating parameter pair is set;
said step of selecting a first operating parameter value further comprises selecting an operating parameter pair by the computer, at which the value of the cost function has an optimum; and
a diagram is generated on the screen by the display device,
in which diagram an interval of the first operating parameter is plotted along a first axis and the interval is selected such that at least some of the permissible first operating parameter values are within the range, and
in which diagram an interval of the second operating parameter is plotted along a second axis, which second axis extends at right angles to the first axis, wherein the interval is selected such that at least some of the permissible second operating parameter values are within the interval, and
in which diagram the selected operating parameter pair is displayed corresponding to the selected operating parameter pair first operating parameter value and second operating parameter value in the diagram.

10. A method in accordance with claim 9, further comprising
presetting a limit value for a second ventilation parameter, wherein the limit value is between a range of allowed second ventilation parameter values and a range of non-allowed second ventilation parameter values;
calculating a set of operating parameter limit value pairs by the computer from a first operating parameter value and a second operating parameter value, wherein the operating parameter limit value pairs are located between a first range of operating parameter pairs and a second range of operating parameter pairs, wherein:
allowed second ventilation parameter values are obtained when operating parameter pairs are set from the first range;
non-allowed ventilation parameter values are obtained when operating parameter pairs are set from the second range;
the step of selecting a first operating parameter value further comprises selecting the operating parameter pair from operating parameter pairs from the first range; and
the set of operating parameter limit value pairs is displayed at positions corresponding to the values of the first operating parameter and the second operating parameter in the diagram.

11. A method in accordance with claim 9, wherein the second operating parameter is selected as the cost function.

12. A method in accordance with claim 9, wherein:
an interval of the values of the cost function is plotted to appear in the diagram along a third axis extending at right angles to the first and second axes; and
the value of the cost function is plotted along the third axis over each permissible operating parameter pair falling in the interval of the first axis and in the interval of the second axis.

13. A method in accordance with claim 9, wherein:
a plurality of lines are formed in the diagram;
a value for the cost function is assigned to each line; and
the value of the cost function assigned to each line is calculated for the operating parameter pairs located on one of the lines.

14. A method in accordance with claim 10, wherein:
a changed limit value is preset;
the changed limit value is located between a range of allowed second ventilation parameter values and a range of non-allowed second ventilation parameter value;

a second set of operating parameter limit value pairs is calculated by the computer from a first operating parameter value and a second operating parameter value;

the operating parameter limit value pairs of the second set are located between a first changed range of operating parameter pairs and a second changed range of operating parameter pairs;

allowed second ventilation parameter values are obtained if operating parameter pairs are set from the first changed range;

non-allowed second ventilation parameter values are obtained if operating parameter pairs are set from the second changed range; and the second set of operating parameter limit value pairs is displayed in the diagram at positions corresponding to the values of the first operating parameter and the second operating parameter.

15. A method in accordance with claim 1, wherein:
the target value range is changed;
the steps of presetting a target value range, calculating permissible first operating parameter values, calculating the values of a preset cost function, selecting a first operating parameter value and outputting the selected first operating parameter value are carried out with the changed target value range after changing the target value range, wherein a second target value is used to calculate permissible changed operating parameter values, so that a changed first operating parameter value is selected; and the selected first operating parameter value and the changed selected first operating parameter value are outputted.

16. A method for selecting the setting of at least one first operating parameter of a ventilation system comprising devices for feeding and removing breathing air to and from a patient, a computer and a display device with a screen, the method comprising the steps of:

presetting a first target value range for a first ventilation parameter;

calculating permissible first operating parameter values by the computer for the at least one operating parameter, so that the first ventilation parameter value is within the target value range if a permissible first operating parameter value is set;

presetting a limit value for a second ventilation parameter, wherein the limit value is located between a range of allowed second ventilation parameter values and a range of non-allowed second ventilation parameter values;

calculating one or more first operating parameter limit values by the computer, wherein the operating parameter limit values are located between a first range of first operating parameter values and a second range of first operating parameter values, so that allowed second ventilation parameter values are obtained if first operating parameter values are set from the first range, and so that non-allowed second ventilation parameter values are obtained if first operating parameter values are set from the second range; and outputting the permissible first operating parameter values, which are within the first range, on the display device;

the settings of a first operating parameter and a second operating parameter are selected;

said step of calculating permissible first operating parameter values, by the computer for the first operating parameter further comprises calculating permissible operating parameter value pairs by the computer for the first operating parameter and the second operating parameter, so that the first ventilation parameter value is within the target value range if a permissible operating parameter pair is set;

said step of calculating one or more first operating parameter limit values further comprises calculating a set of operating parameter limit value pairs by the computer from a first operating parameter value and a second operating parameter value;

the operating parameter limit value pairs are located between a first range of operating parameter pairs and a second range of operating parameter pairs, so that allowed second ventilation parameter values are obtained if operating parameter pairs are set from the first range, and so that non-allowed ventilation parameter values are obtained if operating parameter pairs are set from the second range;

a diagram is generated by the display device on the screen, in which diagram an interval of the first operating parameter is plotted along one first axis, wherein the interval is selected such that at least some of the permissible first operating parameter values are within the interval and in which diagram an interval of the second operating parameter is plotted along a second axis, which extends at right angles to the first axis, wherein the interval is selected such that at least some of the permissible second operating parameter values are within the interval and in which diagram the permissible operating parameter pairs from the first range corresponding to the values of the first operating parameter and of the second operating parameter are displayed in the diagram and in which diagram the set of operating parameter limit value pairs are displayed in the diagram at positions corresponding to the values of the first operating parameter and the second operating parameter.

17. A method in accordance with claim 16, wherein:
a changed limit value is preset for the second ventilation parameter;

the changed limit value is located between a range of allowed second ventilation parameter values and a range of non-allowed second ventilation parameter values;

a second set of operating parameter limit value pairs is calculated by the computer from a first operating parameter value and a second operating parameter value;

the operating parameter limit value pairs of the second set are located between a first changed range of operating parameter pairs and a second changed range of operating parameter pairs, so that allowed second ventilation parameter values are obtained if operating parameter pairs are set from the first changed range, and so that non-allowed second ventilation parameter values are obtained if operating parameter pairs are set from the second changed range; and the second set of operating parameter limit value pairs is displayed at positions corresponding to the values of the first and second operating parameters in the diagram.

18. A method for selecting a setting of an operating parameter of a ventilation system for a patient, the method comprising the steps of:

setting a target value for a first ventilation parameter;

calculating a plurality of target pairs of first and second operating parameter values for first and second operating parameters, each of the target pairs of the operating parameter values corresponds to ventilation at the target value for the first ventilation parameter, the target pairs forming a target ventilation parameter curve;

setting upper and lower limits for a second ventilation parameter;

calculating a plurality of upper limit pairs and lower limit pairs of the first and second operating parameter values for the first and second operating parameters, each of the upper and lower limit pairs of operating parameter values corresponds to ventilation at respective upper and lower limits for the second ventilation parameter, the upper limit pairs forming an upper limit ventilation parameter curve, the lower limit pairs forming an lower limit ventilation parameter curve;

generating operating parameter diagram with the first operating parameter versus the second operating parameter;

superimposing the upper limit ventilation parameter curve, the lower limit ventilation parameter curve and the target ventilation parameter curve onto the diagram of the operating parameters, the diagram forming an allowable operating region between the upper and lower limit ventilation parameter curves;

displaying the operating parameter diagram to an operator of the ventilation system.

19. A method in accordance with claim 18, wherein:

the diagram is a two-dimensional graph with the first and second operating parameters plotted along a first and second axis.

20. A method in accordance with claim 18, wherein:

the diagram has an interval with the first and second operating parameters plotted along a first and second axis, the interval having at least some of the target pairs in the diagram, the target pairs being displayed in the diagram corresponding to the first operating parameter value and the second operating parameter value.

* * * * *